US012691451B2

(12) United States Patent (10) Patent No.: US 12,691,451 B2
Sato et al. (45) Date of Patent: Jul. 28, 2026

(54) TEMPERATURE CONTROL DEVICE

(71) Applicant: Hitachi High-Tech Corporation, Tokyo (JP)

(72) Inventors: Wataru Sato, Tokyo (JP); Nobuyuki Isoshima, Tokyo (JP); Tatsuya Kobari, Tokyo (JP); Masashi Shibahara, Tokyo (JP)

(73) Assignee: Hitachi High-Tech Corporation, Tokyo (JP)

( * ) Notice: Subject to any disclaimer, the term of this patent is extended or adjusted under 35 U.S.C. 154(b) by 665 days.

(21) Appl. No.: 18/018,622

(22) PCT Filed: Sep. 2, 2020

(86) PCT No.: PCT/JP2020/033303
§ 371 (c)(1),
(2) Date: Jan. 30, 2023

(87) PCT Pub. No.: WO2022/049678
PCT Pub. Date: Mar. 10, 2022

(65) Prior Publication Data
US 2023/0294101 A1 Sep. 21, 2023

(51) Int. Cl.
*B01L 7/00* (2006.01)
*B01L 99/00* (2010.01)
(Continued)

(52) U.S. Cl.
CPC ................. *B01L 7/52* (2013.01); *C12M 1/00* (2013.01); *C12M 41/12* (2013.01); *C12Q 1/686* (2013.01);
(Continued)

(58) Field of Classification Search
CPC ......... B01L 2200/025; B01L 2200/147; B01L 2300/0861; B01L 2300/1822; B01L 7/52; C12M 1/00; C12M 41/12; C12Q 1/686
(Continued)

(56) References Cited

U.S. PATENT DOCUMENTS

2002/0072112 A1 6/2002 Atwood et al.
2004/0258568 A1 12/2004 Lurz et al.
(Continued)

FOREIGN PATENT DOCUMENTS

CN 101583708 A 11/2009
CN 102917796 A 2/2013
(Continued)

OTHER PUBLICATIONS

Partial Supplementary European Search Report issued in European Application No. 20952418.0 dated Dec. 20, 2023 (14 pages).
(Continued)

*Primary Examiner* — Lydia Edwards
(74) *Attorney, Agent, or Firm* — Crowell & Moring LLP

(57) ABSTRACT

The purpose of the present invention is to provide a temperature control device (1) capable of changing the temperature of a temperature regulating block (2) rapidly and with high accuracy. A temperature control device (1) according to the present invention is provided with: the temperature regulating block (2), on which a container (5) accommodating a solution (6) can be placed; and a temperature regulating part (3) that is installed so as to contact the temperature regulating block (2) and that changes the temperature of the solution (6), wherein the temperature regulating block (2) is provided with, on the inside thereof, one or a plurality of hollow parts (7).

7 Claims, 8 Drawing Sheets

(51) Int. Cl.

| | |
|---|---|
| *C12M 1/00* | (2006.01) |
| *C12M 1/34* | (2006.01) |
| *C12Q 1/686* | (2018.01) |

(52) U.S. Cl.
CPC . *B01L 2200/147* (2013.01); *B01L 2300/1822* (2013.01)

(58) Field of Classification Search
USPC ...................................................... 435/287.2
See application file for complete search history.

(56) References Cited

U.S. PATENT DOCUMENTS

| | | | |
|---|---|---|---|
| 2008/0003650 | A1 | 1/2008 | Banerji |
| 2008/0274511 | A1 | 11/2008 | Tan et al. |
| 2009/0155765 | A1 | 6/2009 | Atwood et al. |
| 2011/0165628 | A1 | 7/2011 | Verhaar et al. |
| 2013/0143272 | A1 | 6/2013 | Guo et al. |
| 2013/0168074 | A1 | 7/2013 | Higginbotham et al. |
| 2018/0274019 | A1 | 9/2018 | Fukuzawa et al. |
| 2019/0329261 | A1 | 10/2019 | Won et al. |
| 2019/0358637 | A1* | 11/2019 | Chun ................. G01N 21/6408 |
| 2020/0398282 | A1 | 12/2020 | Sato et al. |

FOREIGN PATENT DOCUMENTS

| | | | |
|---|---|---|---|
| CN | 108291184 | A | 7/2018 |
| CN | 108998371 | A | 12/2018 |
| JP | 6-233670 | A | 8/1994 |
| JP | 2009-543064 | A | 12/2009 |
| JP | 2010-502228 | A | 1/2010 |
| JP | 2012-502651 | A | 2/2012 |
| JP | 2014-518758 | A | 8/2014 |
| WO | WO 2019/193806 | A1 | 10/2019 |

OTHER PUBLICATIONS

Japanese-language Office Action issued in Japanese Application No. 2022-546783 dated Jan. 9, 2024 with English translation (5 pages).
International Search Report (PCT/ISA/210) issued in PCT Application No. PCT/JP2020/033303 dated Nov. 10, 2020 with English translation (four (4) pages).
Japanese-language Written Opinion (PCT/ISA/237) issued in PCT Application No. PCT/JP2020/033303 dated Nov. 10, 2020 (four (4) pages).
International Preliminary Report on Patentability (PCT/IPEA/409) issued in PCT Application No. PCT/JP2020/033303 dated Jun. 2, 2021, including Annexes with English translation (16 pages).
Chinese-language Office Action issued in Taiwanese Application No. 110130109 dated Jun. 2, 2022 (seven (7) pages).

* cited by examiner

TEMPERATURE CONTROL DEVICE

TECHNICAL FIELD

The present invention relates to a temperature control device.

BACKGROUND ART

In recent years, genetic testing has come to be used not only in research applications but also in a wide range of applications such as personalized medical care and identification to identify an individual, and it is desired not only to improve the accuracy but also to shorten a test time. In the genetic testing, a sample containing DNA (Deoxyribonucleic acid) is acquired, and then a trace amount of DNA in the sample is amplified and then analyzed. In this manner, a highly accurate test is performed. As a method for amplifying DNA, a PCR (Polymerase Chain Reaction) method is widely used. In the PCR method, a sample solution containing DNA and a solution containing a reagent for amplifying DNA are mixed, and for example, DNA is denatured into a single strand at 94° C., and a complementary strand is synthesized at 60° C. By repeating such temperature changes, DNA can be amplified exponentially by the PCR method.

In genetic testing, it is required to shorten the time required for the reaction and shorten the time required for the test, by changing the temperature of a reaction solution containing the sample and the reagent at a high speed. The temperature of the reaction solution is changed by using a temperature control device such as a thermal cycler. A general temperature control device includes a temperature regulating element such as a Peltier element that controls a temperature change, and a temperature regulating block (also referred to as a "temperature regulating block" below) provided to be in contact with the temperature regulating element. Such a temperature control device performs the PCR method by holding a reaction container accommodating a reaction solution in the temperature regulating block, and controlling the temperature of the temperature regulating block with the temperature regulating element.

The thermal conductivity and the heat capacity of the temperature regulating block affect the speed-up of the temperature change of the reaction solution in the temperature control device. In the general temperature control device, a material having a high thermal conductivity, for example, metal such as aluminum or copper is used for the temperature regulating block. By using the material having a high thermal conductivity for the temperature regulating block, it is possible to efficiently transfer heat generated by the temperature regulating element to the reaction container, and to change the temperature of the reaction solution at a high speed. The heat capacity is a value obtained from the specific heat, density, and volume of the material. When the heat capacity of the temperature regulating block is large, it takes time to change the temperature of the temperature regulating block, and the temperature change of the reaction solution becomes slow.

Examples of conventional temperature control devices are disclosed in PTL 1 and PTL 2. The thermocycling device disclosed in PTL 1 includes a sample holder, a thermal reference, and a heat sink, and one or a plurality of the sample holder, the thermal reference, and the heat sink has a material having a high thermal conductivity. The multiple sample support disclosed in PTL 2 includes a block having a single structure, a series of sample wells in the block, and a series of hollow parts in the block, which are provided between the sample wells. The mass of the block is reduced by the hollow part, and the temperature change is transferred to the sample quickly.

CITATION LIST

Patent Literature

PTL 1: JP 2012-502651 A
PTL 2: JP 2009-543064 A

SUMMARY OF INVENTION

Technical Problem

When the temperature control device performs the genetic testing, if the temperature of the temperature regulating block is not appropriately controlled and the reaction solution containing the sample and the reagent is not controlled to an appropriate temperature, it is not possible to stably amplify DNA, and the reliability of the genetic testing is lowered. In the temperature regulating block, generally, if the thermal conductivity is small even though the heat capacity is small, it is not possible to uniformly transfer the heat of the temperature regulating element to the reaction solution, and it is difficult to control the reaction solution to a temperature obtained by the PCR method. On the other hand, since the temperature regulating block having small dimensions has a small internal temperature difference, the heat of the temperature regulating element can be uniformly transferred to the reaction solution even if the thermal conductivity is small, and a large thermal conductivity is not necessarily required in some cases.

In the temperature regulating block in the conventional temperature control device, values related to the temperature change, such as thermal conductivity, specific heat, and density, are determined by a material to be used. Therefore, it is difficult to appropriately adjust the thermal conductivity and the heat capacity, and there is a problem in changing the temperature of the reaction solution containing the sample and the reagent rapidly and with high accuracy. Therefore, the temperature control device is required to change the temperature of the temperature regulating block rapidly and with high accuracy.

An object of the present invention is to provide a temperature control device capable of changing the temperature of a temperature regulating block rapidly and with high accuracy.

Solution to Problem

A temperature control device according to the present invention is provided with a temperature regulating block on which a container accommodating a solution can be placed, and a temperature regulating part that is installed to contact the temperature regulating block and that changes a temperature of the solution. The temperature regulating block includes one or a plurality of hollow parts therein.

Advantageous Effects of Invention

According to the present invention, it is possible to provide a temperature control device capable of changing the temperature of a temperature regulating block rapidly and with high accuracy.

DESCRIPTION OF EMBODIMENTS

Figure 1:
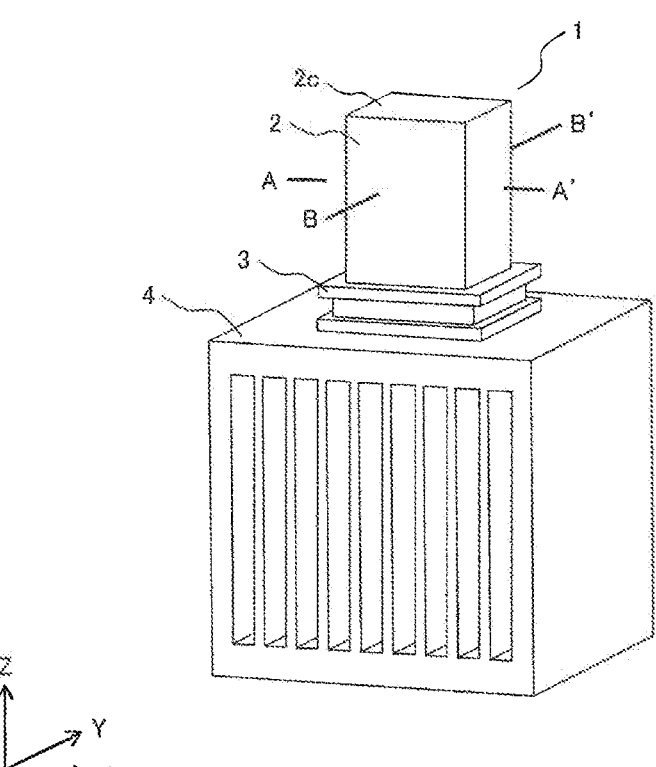
FIG. 1 is a perspective view schematically illustrating a temperature control device according to Embodiment 1 of the present invention.

A temperature control device according to the present invention is provided with a temperature regulating part (temperature regulating part) and a temperature regulating block (temperature regulating block), and the temperature regulating block has a hollow part. In the temperature regulating block, the hollow part reduces the density and the heat capacity, and the temperature can be changed rapidly. In addition, by controlling the heat conduction on the inside of the temperature regulating block by the arrangement of the hollow part, it is possible to change the temperature of the temperature regulating block with high accuracy. Thus, the temperature control device according to the present invention can appropriately control the temperature of the temperature regulating block to control a reaction solution containing a sample and a reagent to an appropriate temperature rapidly and with high accuracy.

Hereinafter, a temperature control device according to embodiments of the present invention will be described with reference to the drawings. In the drawings used in the present specification, the same or corresponding components are denoted by the same reference numerals, and repeated description of these components may be omitted.

Embodiment 1

A temperature control device according to Embodiment 1 of the present invention will be described.

FIG. 1 is a perspective view schematically illustrating the temperature control device according to Embodiment 1 of the present invention. A temperature control device 1 is provided with a temperature regulating block 2 (hereinafter, referred to as a "temperature regulating block 2") and a temperature regulating part 3 (hereinafter, referred to as a "temperature regulating part 3"), and changes the temperature of a reaction solution containing a sample and a reagent.

The temperature regulating block 2 is made of a metal or non-metal material, and can place a reaction container accommodating a reaction solution thereon. The temperature regulating block 2 is placed on the temperature regulating part 3 to contact the temperature regulating part 3. In the temperature regulating block 2, the temperature of the reaction solution in the placed reaction container is controlled by the temperature regulating part 3. In the temperature regulating block 2, for example, the reaction container is placed on an upper surface 2c, or the reaction container is placed in a recess provided in the upper portion. FIG. 1 illustrates the temperature regulating block 2 in which the reaction container is placed on the upper surface 2c. The upper surface 2c of the temperature regulating block 2 is a surface opposite to a surface (lower surface) in contact with the temperature regulating part 3. The schematic shape of the temperature regulating block 2 is not limited to a quadrangular prism shape as illustrated in FIG. 1, and may be any shape such as a polygonal prism shape, a columnar shape, or a cylindrical shape.

The temperature regulating part 3 is a temperature regulating device capable of performing one or both of heating and cooling. The temperature regulating part 3 is installed below the temperature regulating block 2 so as to contact the temperature regulating block 2, and changes the temperature of the reaction solution in the reaction container placed on the temperature regulating block 2. In the present embodiment, the temperature regulating part 3 includes a Peltier element which is a temperature regulating element. The temperature regulating part 3 provided with the Peltier element is provided with a heat dissipation part 4 on the surface opposite to the surface in contact with the temperature regulating block 2. In the present embodiment, a heat dissipation fin is used as the heat dissipation part 4. The temperature regulating part 3 may be provided with a heat pump, a heater heating device, and a cooling device using a cooling structure, in addition to the Peltier element, and may be configured by combining a plurality of these devices.

In order to reduce contact thermal resistance between the temperature regulating block 2 and the temperature regulating part 3 and promote heat transfer, a thermally conductive sheet having elasticity may be installed between the temperature regulating block 2 and the temperature regulating part 3, or a thermally conductive grease may be applied on a portion between the temperature regulating block 2 and the temperature regulating part 3.

The temperature control device 1 controls the temperature of the reaction solution by measuring the temperature of the temperature regulating block 2 with a temperature sensor (not illustrated) such as a thermocouple or a thermistor installed in the temperature regulating block 2, and controlling the output of the temperature regulating part 3 so that the temperature of the temperature regulating block 2 becomes a desired temperature.

In FIG. 1, a direction in which the temperature regulating block 2 and the temperature regulating part 3 are in contact with each other is defined as a Z-direction, and a plane perpendicular to the Z-direction is defined as an XY plane. The Z-direction is a vertical direction (vertical direction).

Figure 2:
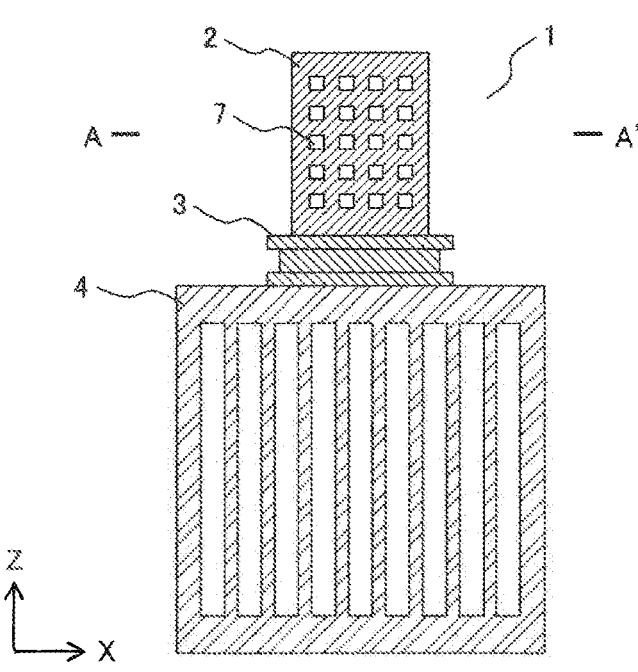
FIG. 2 is a cross-sectional view of the temperature control device taken along line A-A' in FIG. 1.
Figure 3:
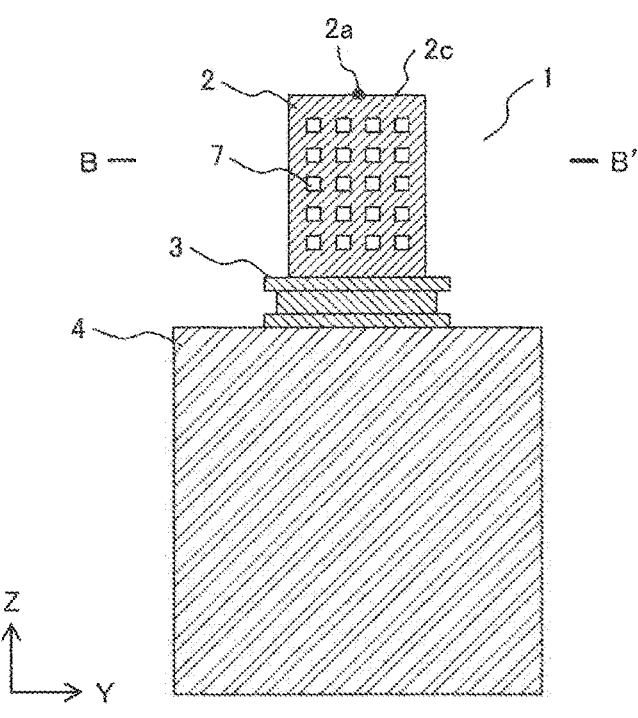
FIG. 3 is a cross-sectional view of the temperature control device taken along line B-B' in FIG. 1.

FIG. 2 is a cross-sectional view of the temperature control device 1 taken along line A-A' in FIG. 1. FIG. 3 is a cross-sectional view of the temperature control device 1 taken along line B-B' in FIG. 1. The line A-A' is a line parallel to an X-direction, and the line B-B' is a line parallel to a Y-direction. FIG. 2 is a cross-sectional view taken along a ZX plane, and FIG. 3 is a cross-sectional view taken along a YZ plane.

The temperature regulating block 2 is provided with a plurality of hollow parts 7 on the inside thereof. The hollow part 7 is a cavity provided at any position on the inside of the temperature regulating block 2. Air exists in the hollow part 7, and the hollow part 7 does not communicate with the outside of the temperature regulating block 2. The hollow part 7 has an effect of reducing the mass of the temperature regulating block 2 and accelerating the temperature change of the temperature regulating block 2. In the example illustrated in FIGS. 2 and 3, the hollow parts 7 are arranged at equal intervals in an orthogonal lattice pattern inside the temperature regulating block 2. The arrangement of the hollow parts 7 inside the temperature regulating block 2 may not be in an orthogonal lattice pattern and may not be at equal intervals. The size, number, and arrangement of the hollow parts 7 are not limited to the examples illustrated in FIGS. 2 and 3, and can be randomly determined.

Since the temperature regulating block 2 is provided with the hollow part 7, the density is small, the heat capacity is small, and the temperature change is fast as compared with a solid temperature regulating block 2 without the hollow part 7.

The density of the temperature regulating block 2 decreases as the volume occupied by the hollow part 7 increases. For example, assuming that the ratio of the volume of the hollow part 7 to the temperature regulating block 2 is 50%, in the temperature regulating block 2, the ratio of the volume of the material forming the temperature regulating block 2 is 50%, and the ratio of the volume of air existing in the hollow part 7 is the remaining 50%. The density of the temperature regulating block 2 is calculated from the density of the material forming the temperature regulating block 2 and the density of the air existing in the hollow part 7. However, since the density of air is much smaller than the density of the material forming the temperature regulating block 2, the density of the temperature regulating block 2 can be obtained only from the density of the material forming the temperature regulating block 2. Therefore, the density of the temperature regulating block 2 decreases to 50% of the apparent density of the temperature regulating block 2. The apparent density is the density of the temperature regulating block 2 when it is assumed that the hollow part 7 is not provided, and is the density calculated from the size of the outer shape of the temperature regulating block 2 and the mass of the solid temperature regulating block 2 not provided with the hollow part 7.

The heat capacity of the temperature regulating block 2 decreases as the density of the temperature regulating block 2 decreases. The temperature change of the temperature regulating block 2 by the action of the temperature regulating part 3 is accelerated by the decrease in the heat capacity. When the ratio of the volume of the hollow part 7 to the temperature regulating block 2 is 50% and the density of the temperature regulating block 2 decreases to 50% of the apparent density, the heat capacity of the temperature regulating block 2 decreases to 50% being the ratio of the solid temperature regulating block 2 without the hollow part 7. Then, the temperature change of the temperature regulating block 2 is 50% faster than the temperature change of the solid temperature regulating block 2 without the hollow part 7.

In the present embodiment, the hollow part 7 does not communicate with the outside of the temperature regulating block 2, and thus the surface area of the temperature regulating block 2 does not increase even if the hollow part 7 is provided. When the surface area of the temperature regulating block 2 increases, heat exchange with surrounding air is promoted, and the temperature change may be suppressed. However, in the temperature control device 1 according to the present embodiment, since the temperature regulating block 2 is provided with the hollow part 7 without increasing the surface area, it is possible to suppress the heat exchange between the temperature regulating block 2 and the surrounding air, and it is possible to change the temperature of the temperature regulating block 2 rapidly.

Figure 4:
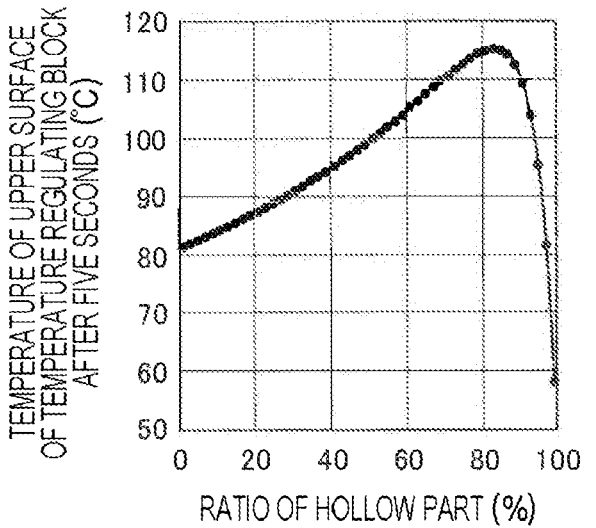
FIG. 4 is a diagram illustrating an example of a result of obtaining a temperature change of a temperature regulating block by a heat conduction analysis.

FIG. 4 is a diagram illustrating an example of a result of obtaining the temperature change of the temperature regulating block 2 by a heat conduction analysis. FIG. 4 illustrates a result obtained by calculating the temperature change at an upper surface measurement point 2a of the temperature regulating block 2 when an amount of heat of 10 W is input from the bottom surface to the aluminum temperature regulating block 2 having a width of 10 mm, a depth of 10 mm, and a height of 20 mm. As illustrated in FIG. 3, the upper surface measurement point 2a is a center point of an upper surface 2c of the temperature regulating block 2 (a surface opposite to a surface in contact with the temperature regulating part 3). In FIG. 4, the horizontal axis represents the ratio of the volume of the hollow part 7 to the temperature regulating block 2, and the vertical axis represents the temperature at the upper surface measurement point 2a after 5 seconds from the input of the amount of heat to the temperature regulating block 2.

As the ratio of the volume of the hollow part 7 increases, the temperature at the upper surface measurement point 2a of the temperature regulating block 2 after 5 seconds increases until the ratio of the hollow part 7 reaches about 85%. However, when the ratio of the hollow part 7 exceeds 85%, the temperature of the upper surface measurement point 2a decreases as the ratio of the hollow part 7 increases. This is because the ratio of the hollow part 7 is increased, so that the thermal conductivity of the temperature regulating block 2 is decreased, and the temperature of the upper surface measurement point 2a of the temperature regulating block 2 is less likely to rise. Therefore, by setting the ratio of the volume of the hollow part 7 in the temperature regulating block 2 to an appropriate value in accordance with the dimensions and the material of the temperature regulating block 2, it is possible to change the temperature of the temperature regulating block 2 rapidly.

The temperature regulating block 2 provided with the hollow part 7 is desirably made of a material having a high thermal conductivity. For example, by forming the temperature regulating block 2 with metal such as aluminum, copper, or magnesium, or an alloy thereof, it is possible to increase the thermal conductivity while reducing the heat capacity of the temperature regulating block 2. The material of the temperature regulating block 2 is not limited to metal, and may be a nonmetallic material having a high thermal conductivity, such as aluminum nitride or carbon fiber.

The hollow part 7 provided in the temperature regulating block 2 can have any shape such as a rectangular parallelepiped shape, a polygonal columnar shape, a columnar shape, or a spherical shape. All of the plurality of hollow parts 7 may not be isolated, and all or some of the plurality of hollow parts 7 may communicate with each other. In addition, the hollow part 7 may communicate with the outside of the temperature regulating block 2 from an opening provided on the surface of the temperature regulating block 2. The hollow part 7 communicating with the outside of the temperature regulating block 2 can be easily formed.

The fluid existing in the hollow part 7 may not be air, and may be a fluid other than air, for example, an inert gas such as nitrogen or a liquid (for example, oil or water). A heat insulating material made of a resin material or a porous material may be disposed in the hollow part 7. The inside of the hollow part 7 may be a vacuum. When the inside of the hollow part 7 is filled with an inert gas, it is possible to prevent oxidation of the surface of the hollow part 7. When the hollow part 7 is filled with a liquid, it is possible to adjust the heat capacity of the temperature regulating block 2 by the liquid, and it is possible to efficiently perform the heat exchange to accelerate the temperature change of the temperature regulating block 2. When the inside of the hollow part 7 is filled with a heat insulating material or evacuated, it is possible to suppress the heat conduction to the outside of the temperature regulating block 2 and to accelerate the temperature change of the temperature regulating block 2.

As described above, the size, number, and arrangement of the hollow parts 7 can be randomly determined. Therefore, in the temperature control device 1 according to the present embodiment, by changing the density (arrangement density) at which the hollow part 7 is arranged in accordance with the position inside the temperature regulating block 2, it is possible to control the heat conduction inside the temperature regulating block 2 and control the temperature change of the temperature regulating block 2 in accordance with the position inside the temperature regulating block 2. Accordingly, it is possible to change the temperature of the temperature regulating block 2 with high accuracy.

The hollow part 7 can be formed by any method. For example, the hollow part 7 can be formed by making a hole in a lump of material forming the temperature regulating block 2 or by installing a partition member (partition wall) in a space inside a box-shaped member constituting the temperature regulating block 2. As the partition member, a member having any shape such as a plate-like member having a lattice shape or a columnar member having a prismatic shape or a cylindrical shape can be used. Note that the temperature regulating block 2 provided with the hollow part 7 that does not communicate with the outside can be formed by any method such as a method of joining a plurality of portions of the temperature regulating block 2, which have depressions that constitute the hollow part 7, to each other.

In the temperature control device 1 according to the present embodiment, since the temperature regulating block 2 is provided with the hollow part 7 on the inside thereof, it is possible to change the temperature of the temperature regulating block 2 rapidly and with high accuracy.

Embodiment 2

A temperature control device 1 according to Embodiment 2 of the present invention will be described. In the temperature control device 1 according to the present embodiment, a plurality of hollow parts 7 provided in the temperature regulating block 2 form a honeycomb structure.

Figure 5:
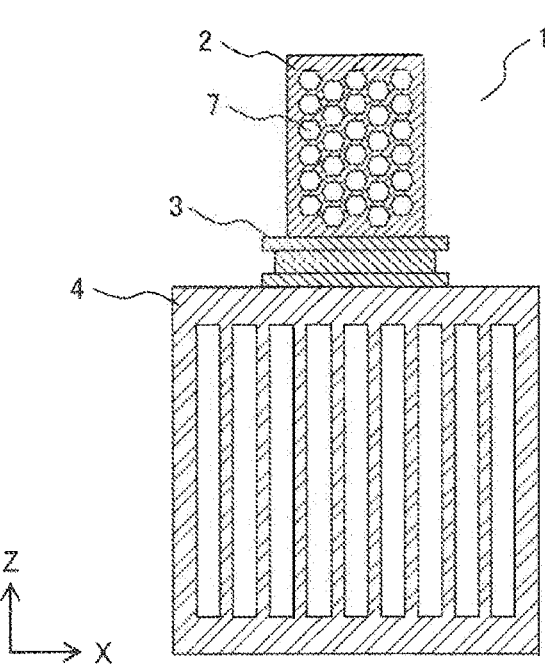
FIG. 5 is a cross-sectional view schematically illustrating a temperature control device according to Embodiment 2 of the present invention.

FIG. 5 is a cross-sectional view schematically illustrating the temperature control device 1 according to Embodiment 2 of the present invention, and is a cross-sectional view at the same position as that in FIG. 2. The plurality of hollow parts 7 provided inside the temperature regulating block 2 have a regular hexagonal column shape and are arranged so as to form a honeycomb structure.

When the hollow part 7 forms a honeycomb structure inside the temperature regulating block 2, the density decreases, the heat capacity decreases, and the strength can be maintained against the pressing pressure in the Z-direction. The temperature regulating block 2 may be pressed in the Z-direction toward the temperature regulating part 3 with a fastener or the like in order to reduce contact thermal resistance with the temperature regulating part 3. When the hollow part 7 forms the honeycomb structure, even if the temperature regulating block 2 is pressed in the Z-direction toward the temperature regulating part 3, the temperature regulating block 2 can maintain the strength without being crushed.

In the temperature control device 1 according to the present embodiment, it is possible to change the temperature of the temperature regulating block 2 rapidly and with high accuracy, and to reduce the contact thermal resistance between the temperature regulating block 2 and the temperature regulating part 3.

Embodiment 3

A temperature control device 1 according to Embodiment 3 of the present invention will be described. In the temperature control device 1 according to the present embodiment, the temperature regulating block 2 is provided with, on an inside thereof, a plurality of regions having different arrangement densities of the hollow parts 7.

Figure 6:
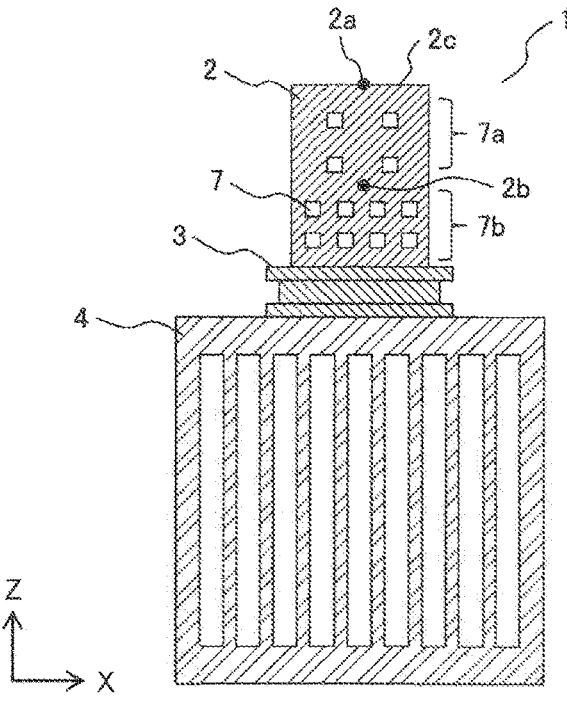
FIG. 6 is a cross-sectional view schematically illustrating a temperature control device according to Embodiment 3 of the present invention.

FIG. 6 is a cross-sectional view schematically illustrating the temperature control device 1 according to Embodiment 3 of the present invention, and is a cross-sectional view at the same position as that in FIG. 2. In the present embodiment, the temperature regulating block 2 is provided with, on the inside thereof, two regions having different arrangement densities of the hollow parts 7. That is, the temperature regulating block 2 is provided with, on the inside thereof, a region 7a having a low arrangement density of the hollow parts 7 and a region 7b having a high arrangement density of the hollow parts 7.

In the example illustrated in FIG. 6, the arrangement density of the hollow parts 7 varies depending on the distance from the temperature regulating part 3, that is, in the vertical direction (Z-direction) of the temperature regulating block 2. The region 7b having a high arrangement density of the hollow parts 7 is located at a position close to the temperature regulating part 3 in the temperature regulating block 2, that is, a position adjacent to the temperature regulating part 3. The region 7a having a low arrangement density of the hollow parts 7 is located at a position far from the temperature regulating part 3 in the temperature regulating block 2, that is, a position between the region 7b having a high arrangement density of the hollow parts 7 and the upper surface 2c of the temperature regulating block 2 (a position adjacent to the upper surface 2c of the temperature regulating block 2). Therefore, in the example illustrated in FIG. 6, the region 7b having a high arrangement density of the hollow parts 7 is located at the lower portion of the temperature regulating block 2, and the region 7a having a low arrangement density of the hollow parts 7 is located at the upper portion of the temperature regulating block 2.

In the temperature control device 1 according to the present embodiment, by changing the arrangement density of the hollow parts 7 inside the temperature regulating block 2, it is possible to change the density (that is, the heat capacity) and the thermal conductivity of the temperature regulating block 2 depending on the position inside the temperature regulating block 2.

For example, as in the example illustrated in FIG. 6, in the temperature regulating block 2, by changing the arrangement density of the hollow parts 7 between a region close to the temperature regulating part 3 and a region far from the temperature regulating part 3, it is possible to accelerate the temperature change of the temperature regulating block 2 and to uniformly transfer the heat of the temperature regulating part 3 to the reaction solution in the reaction container placed on the temperature regulating block 2.

In the region 7b having a high arrangement density of the hollow parts 7, the temperature regulating block 2 has a smaller density and a smaller heat capacity than the region 7a having a low arrangement density of the hollow parts 7. Thus, the temperature change is faster. Therefore, it is possible to accelerate the temperature change at a central measurement point 2b of the temperature regulating block 2. The central measurement point 2b is a central position inside the temperature regulating block 2 between the region 7a having a low arrangement density of the hollow part 7 and the region 7b having a high arrangement density of the hollow part 7.

In the region 7a having a low arrangement density of the hollow parts 7, the temperature regulating block 2 has a larger density and a larger heat capacity than the region 7b having a high arrangement density of the hollow parts 7, but the temperature regulating block 2 has a larger thermal conductivity because the ratio of the volume of the hollow parts 7 is low. Therefore, it is possible to reduce the temperature difference between the central measurement point 2b and the upper surface measurement point 2a of the temperature regulating block 2 and to reduce the temperature difference inside the temperature regulating block 2. Therefore, the temperature inside the temperature regulating block 2 becomes uniform, and it is possible to uniformly transfer the heat of the temperature regulating part 3 to the reaction solution in the reaction container placed on the temperature regulating block 2.

Note that the region 7b having a high arrangement density of the hollow parts 7 may be located above the temperature regulating block 2, and the region 7a having a low arrangement density of the hollow parts 7 may be located below the temperature regulating block 2. The arrangement density of the hollow parts 7 can be determined in accordance with the uniformity of the temperature and the rate of temperature change required for the temperature regulating block 2. For example, the arrangement density of the hollow parts 7 can be determined in consideration of the balance between the uniformity of the temperature at the lower portion of the temperature regulating block 2 (position close to the temperature regulating part 3) and the rate of temperature change in the entire temperature regulating block 2.

Further, the arrangement density of the hollow parts 7 may vary in the horizontal plane direction (in the XY plane) of the temperature regulating block 2. In the temperature regulating block 2, a plurality of reaction containers may be placed in the XY plane. At this time, by changing the arrangement density of the hollow parts 7 in the XY plane, it is possible to prevent the temperatures of the reaction containers can be prevented from being different from each other.

Note that the number of regions having different arrangement densities of the hollow parts 7 is not limited to two, and may be three or more.

In the temperature control device 1 according to the present embodiment, by changing the arrangement density of the hollow parts 7 inside the temperature regulating block 2, it is possible to randomly change the density (that is, the heat capacity) and the thermal conductivity of the temperature regulating block 2 at the position inside the temperature regulating block 2. Therefore, the temperature control device 1 according to the present embodiment can adjust the temperature distribution of the temperature regulating block 2, and can change the temperature of the temperature regulating block 2 rapidly and with high accuracy.

Embodiment 4

A temperature control device 1 according to Embodiment 4 of the present invention will be described. In the temperature control device 1 according to the present embodiment, the temperature regulating block 2 is provided with one or a plurality of recesses at the upper portion. A reaction container accommodating a reaction solution is placed in the recess.

Figure 7:
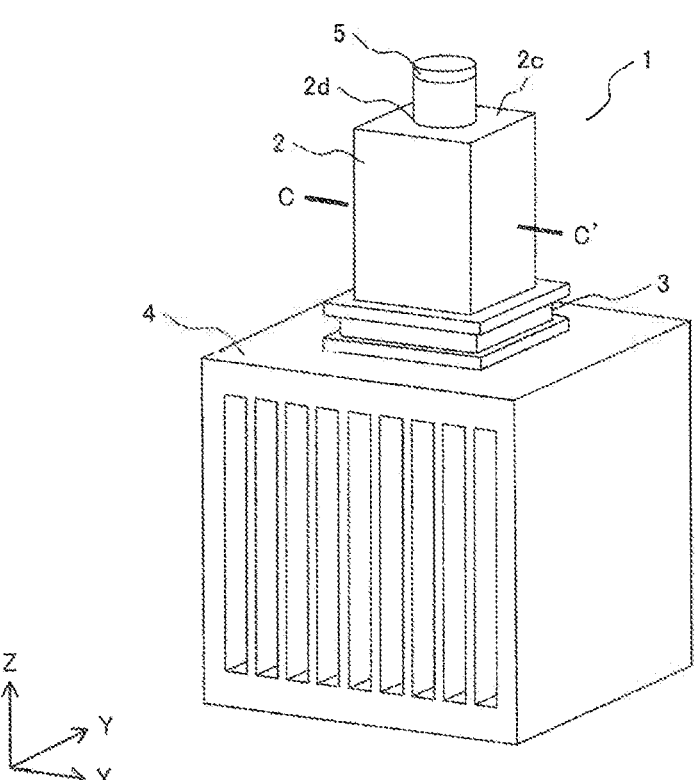
FIG. 7 is a perspective view schematically illustrating a temperature control device according to Embodiment 4 of the present invention.
Figure 8:
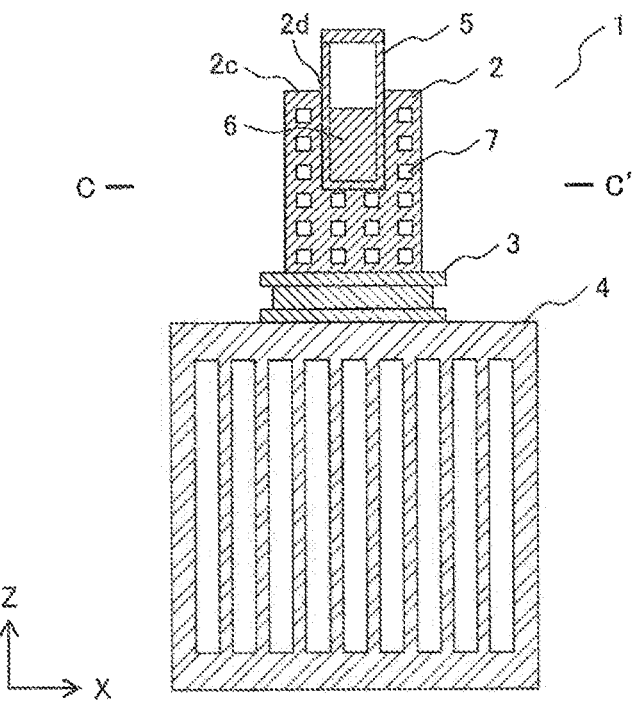
FIG. 8 is a cross-sectional view of the temperature control device taken along line C-C' in FIG. 7.

FIG. 7 is a perspective view schematically illustrating the temperature control device 1 according to Embodiment 4 of the present invention. FIG. 8 is a cross-sectional view of the temperature control device 1 taken along line C-C' in FIG. 7. The line C-C' is a line parallel to the X-direction. FIG. 8 is a cross-sectional view taken along the ZX plane. In the example illustrated in FIGS. 7 and 8, the temperature regulating block 2 is provided with one recess 2d at the upper portion. The reaction container 5 accommodating the reaction solution 6 is placed in the recess 2d. The temperature regulating block 2 is provided with, on the inside thereof, a plurality of hollow parts 7, for example, similarly to Embodiment 1 (FIG. 2).

In the temperature control device 1 according to the present embodiment, the temperature regulating block 2 is provided with the recess 2d on which the reaction container 5 is placed and the hollow part 7. Thus, it is possible to increase the temperature change on the inner wall surface of the recess 2d by the hollow part 7, and to effectively transfer the heat generated in the temperature regulating part 3 to the reaction solution 6 accommodated in the reaction container 5.

Embodiment 5

A temperature control device 1 according to Embodiment 5 of the present invention will be described. In the temperature control device 1 according to the present embodiment, a plurality of hollow parts 7 provided inside the temperature regulating block 2 communicate with each other.

Figure 9:
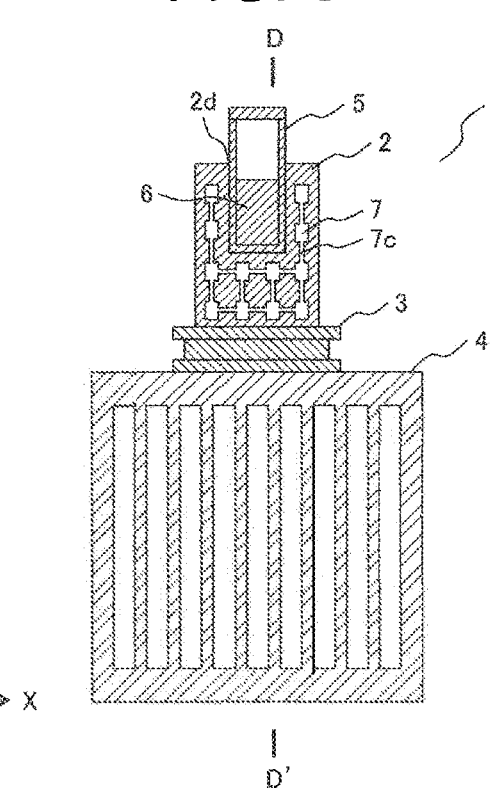
FIG. 9 is a cross-sectional view schematically illustrating a temperature control device according to Embodiment 5 of the present invention.

FIG. 9 is a cross-sectional view schematically illustrating the temperature control device 1 according to Embodiment 5 of the present invention, and is a cross-sectional view at the same position as that in FIG. 8. In the present embodiment, the plurality of hollow parts 7 provided inside the temperature regulating block 2 communicate with each other by a connection part 7c. The connection part 7c is a cavity that connects the plurality of hollow parts 7 to each other. FIG. 9 illustrates, as an example, the temperature regulating block 2 provided with the recess 2*d*, which has been described in Embodiment 4 (FIG. 8).

Figure 10:
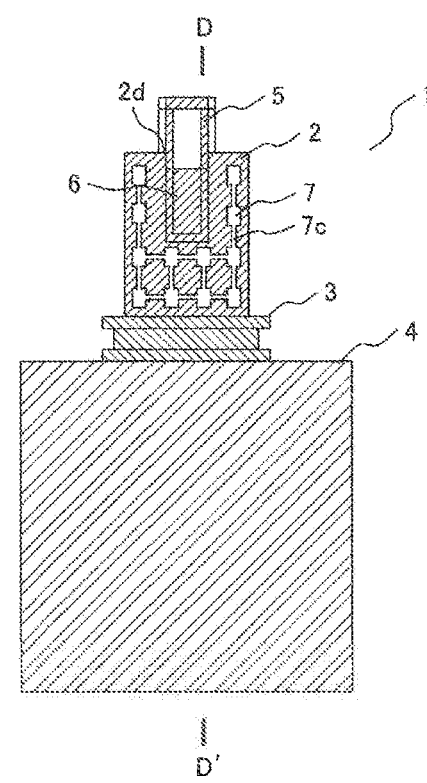
FIG. 10 is a cross-sectional view of the temperature control device taken along line D-D' in FIG. 9.

FIG. 10 is a cross-sectional view of the temperature control device 1 taken along line D-D' in FIG. 9. The line D-D' is a line parallel to the Z-direction. FIG. 10 is a cross-sectional view taken along the YZ plane.

As illustrated in FIGS. 9 and 10, the hollow parts 7 communicate with each other by connection parts 7*c* in the X-direction, the Y-direction, and the Z-direction. The hollow parts 7 communicating with each other by the connection parts 7*c* are easily formed. In addition, when the hollow parts 7 communicate with each other by the connection part 7*c*, it is possible to easily perform an operation of filling the inside of the hollow part 7 with a fluid (for example, air, inert gas, or liquid) or making a vacuum. Furthermore, when the inside of the hollow part 7 is filled with a fluid, it is possible to uniformly fill the hollow part 7 connected by the connection part 7*c*. In the example illustrated in FIGS. 9 and 10, the size (cross-sectional area) of the connection part 7*c* is smaller than the size (cross-sectional area) of the hollow part 7.

In the temperature regulating block 2, all the hollow parts 7 may not communicate with each other by the connection part 7*c*, and only specific parts among the hollow parts 7 may communicate with each other by the connection part 7*c*. The size (cross-sectional area) of the connection part 7*c* can be freely determined, and may be equal to or different from the size (cross-sectional area) of the hollow part 7. For example, a configuration in which the size of the connection part 7*c* is set to be equal to the size of the hollow part 7, and the hollow part 7 is set to communicate with the temperature regulating block 2 without changing the size of the hollow part 7 may be made.

Embodiment 6

A temperature control device 1 according to Embodiment 6 of the present invention will be described. In the temperature control device 1 according to the present embodiment, the plurality of hollow parts 7 provided inside the temperature regulating block 2 communicate with each other and communicate with the outside of the temperature regulating block 2.

Figure 11:
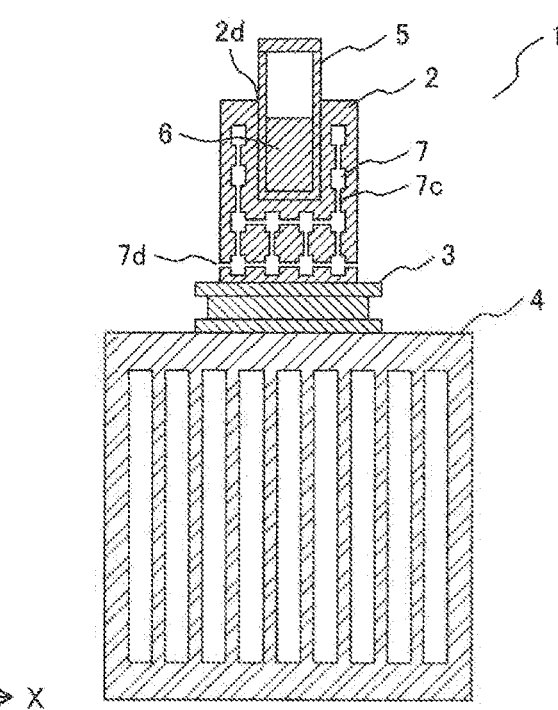
FIG. 11 is a cross-sectional view schematically illustrating a temperature control device according to Embodiment 6 of the present invention.

FIG. 11 is a cross-sectional view schematically illustrating the temperature control device 1 according to Embodiment 6 of the present invention, and is a cross-sectional view at the same position as that in FIG. 9. In the present embodiment, the temperature regulating block 2 is provided with an opening 7*d* on the surface. Note that FIG. 11 illustrates, as an example, the temperature regulating block 2 provided with a recess 2*d*, which has been described in Embodiment 4 (FIG. 8).

The plurality of hollow parts 7 provided inside the temperature regulating block 2 communicate with each other by the connection part 7*c*, and communicate with the outside of the temperature regulating block 2 from the opening 7*d*. The opening 7*d* can be provided at any position on the surface of the temperature regulating block 2.

When the hollow part 7 communicates with the outside of the temperature regulating block 2, it is possible to easily form the hollow part 7 as described in Embodiment 1. Furthermore, it is possible to easily fill the hollow part 7 with a fluid (for example, inert gas or liquid), dispose a heat insulating material, and perform an operation of vacuuming the inside of the hollow part 7.

Embodiment 7

A temperature control device 1 according to Embodiment 7 of the present invention will be described. In the temperature control device 1 according to the present embodiment, the temperature regulating block 2 is provided with, on an inside thereof, a plurality of regions having different arrangement densities of the hollow parts 7.

Figure 12:
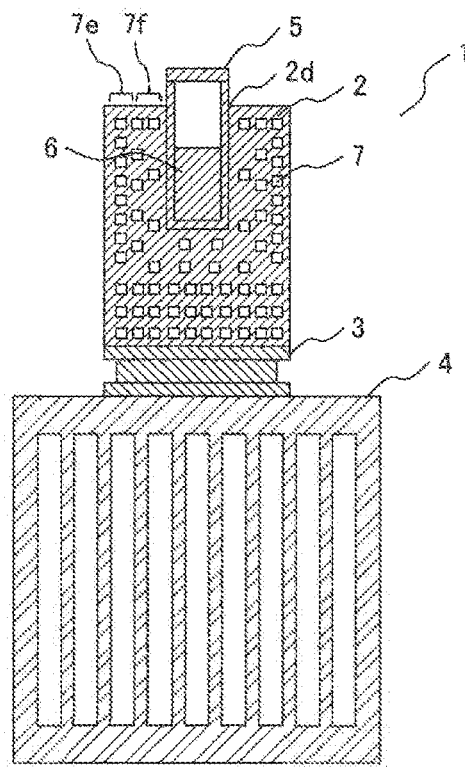
FIG. 12 is a cross-sectional view schematically illustrating a temperature control device according to Embodiment 7 of the present invention.
Figure 12:
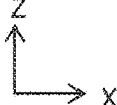

FIG. 12 is a cross-sectional view schematically illustrating the temperature control device 1 according to Embodiment 7 of the present invention, and is a cross-sectional view at the same position as that in FIG. 8. In the present embodiment, the temperature regulating block 2 is provided with, on the inside thereof, two regions having different arrangement densities of the hollow parts 7. That is, the temperature regulating block 2 is provided with, on the inside thereof, a region 7*e* having a high arrangement density of the hollow parts 7 and a region 7*f* having a low arrangement density of the hollow parts 7. Note that FIG. 12 illustrates, as an example, the temperature regulating block 2 provided with a recess 2*d*, which has been described in Embodiment 4 (FIG. 8).

In the example illustrated in FIG. 12, the arrangement density of the hollow parts 7 varies depending on the distance from the recess 2*d*, that is, the distance from the reaction container 5 accommodating the reaction solution 6. In other words, the arrangement density of the hollow parts 7 varies in the horizontal plane direction (in the XY plane) of the temperature regulating block 2. The region 7*f* having a low arrangement density of the hollow parts 7 is located at a position close to the recess 2*d* (or the reaction container 5) in the temperature regulating block 2, that is, a position adjacent to the recess 2*d* (or the reaction container 5). The region 7*e* having a high arrangement density of the hollow parts 7 is high is located at a position far from the recess 2*d* (or the reaction container 5) in the temperature regulating block 2, that is, a position adjacent to the region 7*f* having a low arrangement density of the hollow parts 7. Therefore, the region 7*f* having a low arrangement density of the hollow part 7 is located closer to the recess 2*d* (or the reaction container 5) than the region 7*e* having a high arrangement density of the hollow part 7. In the example illustrated in FIG. 12, the region 7*f* having a low arrangement density of the hollow parts 7 is located at the central portion of the temperature regulating block 2, and the region 7*e* having a high arrangement density of the hollow parts 7 is located at the peripheral portion of the temperature regulating block 2.

In the temperature control device 1 according to the present embodiment, by locating the region 7*f* having a low arrangement density of the hollow parts 7 at the position close to the reaction containers, the thermal conductivity of the temperature regulating block 2 is large at the position close to the reaction container 5. Thus, it is possible to uniformly maintain the temperature of the contact surface between the temperature regulating block 2 and the reaction container 5 and to uniformly transfer the heat of the temperature regulating part 3 to the reaction solution 6 accommodated in the reaction container 5. In addition, since the region 7*e having a high arrangement density of the hollow part 7 is located far from the reaction container 5, at a position far from the reaction container 5, the density of the temperature regulating block 2 decreases, the heat capacity decreases, and the temperature change increases. Further, the region 7***e* having a high arrangement density of the hollow parts 7 is located at the peripheral portion of the temperature regulating block 2, and to reduce the thermal conductivity of the temperature regulating block 2 at this position. Therefore, in the temperature regulating block 2, since the thermal resistance from the region 7*f* having a low arrangement density of the hollow parts 7 to the region 7*e* having a high arrangement density of the hollow parts 7 increases, it is possible to suppress heat dissipation from the surface to the outside air, and the temperature change becomes faster.

Embodiment 8

A temperature control device 1 according to Embodiment 8 of the present invention will be described. In the temperature control device 1 according to the present embodiment, the temperature regulating block 2 is provided with, on an inside thereof, a plurality of regions having different arrangement densities of the hollow parts 7.

Figure 13:
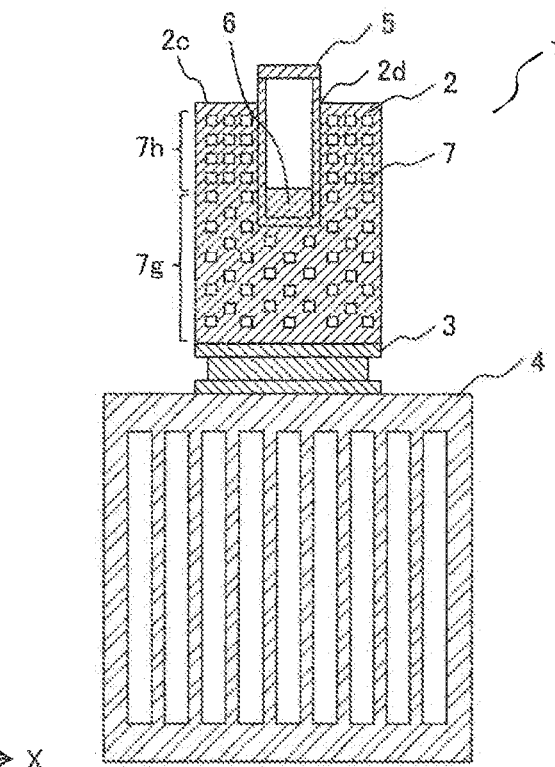
FIG. 13 is a cross-sectional view schematically illustrating a temperature control device according to Embodiment 8 of the present invention.

FIG. 13 is a cross-sectional view schematically illustrating the temperature control device 1 according to Embodiment 8 of the present invention, and is a cross-sectional view at the same position as that in FIG. 8. In the present embodiment, the temperature regulating block 2 is provided with, on the inside thereof, two regions having different arrangement densities of the hollow parts 7. That is, the temperature regulating block 2 is provided with, on the inside thereof, a region 7g having a low arrangement density of the hollow parts 7 and a region 7h having a high arrangement density of the hollow parts 7. Note that FIG. 12 illustrates, as an example, the temperature regulating block 2 provided with a recess 2d, which has been described in Embodiment 4 (FIG. 8).

In the example illustrated in FIG. 13, the arrangement density of the hollow parts 7 is different between portions above and below the position of the liquid level of the reaction solution 6 accommodated in the reaction container 5 placed in the recess 2d. The region 7g having a low arrangement density of the hollow parts 7 is located below the position of the liquid level of the reaction solution 6 accommodated in the reaction container 5 in the temperature regulating block 2. The region 7h having a high arrangement density of the hollow parts 7 is located above the position of the liquid level of the reaction solution 6 in the temperature regulating block 2. Therefore, in the example illustrated in FIG. 13, the region 7g having a low arrangement density of the hollow parts 7 is located at the lower portion of the temperature regulating block 2, and the region 7h having a high arrangement density of the hollow parts 7 is located at the upper portion of the temperature regulating block 2.

Note that the position of the liquid level of the reaction solution 6 accommodated in the reaction container 5 varies depending on the reaction container 5 and the reaction solution 6, but an approximate position can be determined in advance. Therefore, the position of a boundary in the vertical direction (Z-direction) between the region 7g having a low arrangement density of the hollow parts and the region 7h having a high arrangement density of the hollow parts can be determined in advance as the approximate position of the liquid level of the reaction solution 6 based on information on the reaction container 5 and the reaction solution 6.

In the present embodiment, the region 7h having a high arrangement density of the hollow parts 7 is a region in which the ratio of the volume of the hollow part 7 in the temperature regulating block 2 is large, the thermal conductivity of the temperature regulating block 2 decreases, and the temperature change of the temperature regulating block 2 is slow. For example, the region 7h having a high arrangement density of the hollow parts 7 is a region in which the ratio of the volume of the hollow part 7 in the temperature regulating block 2 exceeds 85% and the thermal conductivity of the temperature regulating block 2 decreases as illustrated in FIG. 4.

In the temperature control device 1 according to the present embodiment, the temperature regulating block 2 has the region 7g having a low arrangement density of the hollow parts 7 below the position of the liquid level of the reaction solution 6, and the thermal conductivity is large and the temperature change is fast. Thus, it is possible to transfer the heat of the temperature regulating part 3 quickly to the reaction solution 6. On the other hand, since the temperature regulating block 2 has the region 7h having a high arrangement density of the hollow parts 7 above the position of the liquid level of the reaction solution 6, and the thermal conductivity is small and the temperature change is slow. Thus, it is possible to suppress the heat dissipation from the upper surface 2c of the temperature regulating block 2 and to further accelerate the temperature change of the entire temperature regulating block 2.

Embodiment 9

A temperature control device 1 according to Embodiment 9 of the present invention will be described. In the temperature control device 1 according to the present embodiment, the temperature regulating block 2 is provided with one or a plurality of hollow parts 7 on the inside thereof. The hollow part 7 has a tubular shape extending in the Z-direction (vertical direction), and can have any shape such as a rectangular cylindrical shape or a cylindrical shape.

Figure 14:
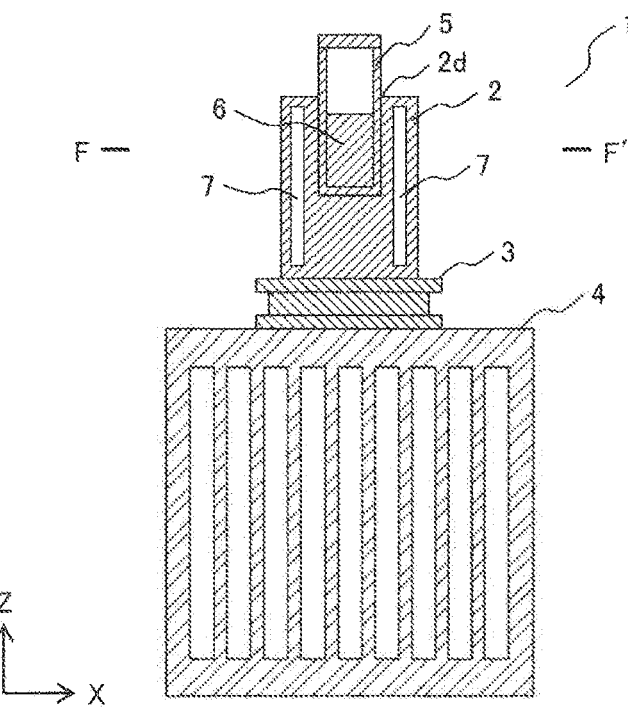
FIG. 14 is a cross-sectional view schematically illustrating a temperature control device according to Embodiment 9 of the present invention.

FIG. 14 is a cross-sectional view schematically illustrating the temperature control device 1 according to Embodiment 9 of the present invention, and is a cross-sectional view at the same position as that in FIG. 8. FIG. 14 illustrates, as an example, the temperature regulating block 2 provided with one cylindrical hollow part 7 on the inside thereof. The cylindrical hollow part 7 is provided at the peripheral portion (outer peripheral portion) of the temperature regulating block 2. Note that FIG. 14 illustrates, as an example, the temperature regulating block 2 provided with the recess 2d, which has been described in Embodiment 4 (FIG. 8).

Figure 15:
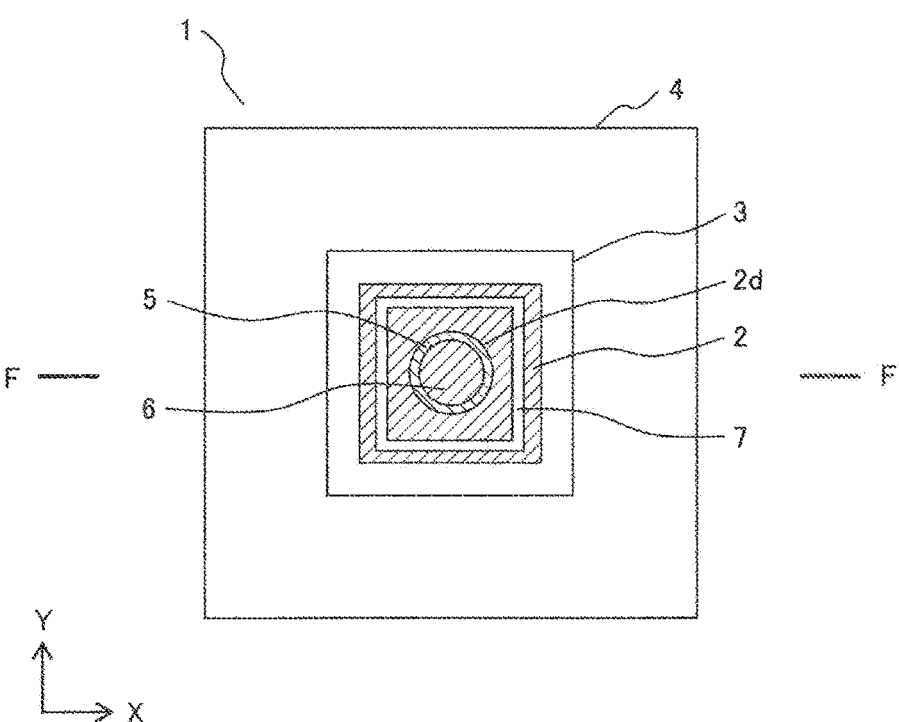
FIG. 15 is a cross-sectional view of the temperature control device on a horizontal plane passing through line F-F' in FIG. 14.

FIG. 15 is a cross-sectional view of the temperature control device 1 on the horizontal plane (XY plane) passing through a line F-F' in FIG. 14. The hollow part 7 has a rectangular tube shape and is provided at a peripheral portion of the temperature regulating block 2. The cylindrical hollow part 7 surrounds the periphery of the recess 2d and surrounds the periphery of the reaction container 5 placed in the recess 2d.

In the temperature control device 1 according to the present embodiment, since the temperature regulating block 2 is provided with the cylindrical hollow part 7 surrounding the periphery of the recess 2d (or the reaction container 5), the thermal conductivity from the recess 2d to the outside of the temperature regulating block 2 decreases, the thermal resistance increases, and it is possible to suppress the heat dissipation from the surface to the outside air. Therefore, the temperature regulating block 2 can suppress the amount of heat dissipation from the side surface, and can further accelerate the temperature change of the entire temperature regulating block 2.

Embodiment 10

A temperature control device 1 according to Embodiment 10 of the present invention will be described. In the temperature control device 1 according to the present embodiment, the temperature regulating block 2 is provided with a plurality of hollow parts 7 at a lower portion in contact with the temperature regulating part 3.

Figure 16:
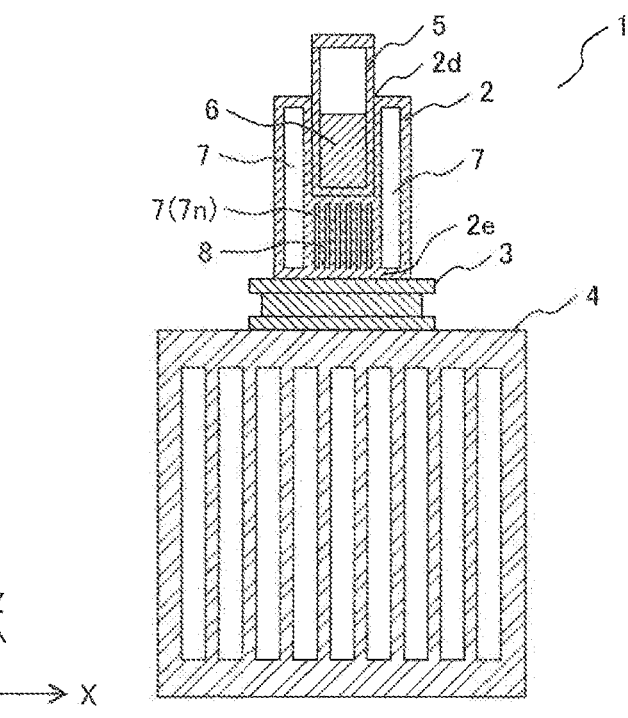
FIG. 16 is a cross-sectional view schematically illustrating a temperature control device according to Embodiment 10 of the present invention.

FIG. 16 is a cross-sectional view schematically illustrating the temperature control device 1 according to Embodiment 10 of the present invention, and is a cross-sectional view at the same position as that in FIG. 8. Note that, FIG. 16 illustrates, as an example, the temperature regulating block 2 also including the cylindrical hollow part 7 surrounding the periphery of the recess 2*d* (or the reaction container 5) described in Embodiment 9 (FIG. 14).

In the temperature control device 1 according to the present embodiment, the temperature regulating block 2 is provided with the recess 2*d* described in Embodiment 4 (FIG. 8). The reaction container 5 accommodating the reaction solution 6 is placed in the recess 2*d*. The temperature regulating block 2 is provided with a plurality of hollow parts 7 (7*n*) at the lower portion in contact with the temperature regulating part 3, more specifically, between the bottom surface 2*e* in contact with the temperature regulating part 3 and the lower portion of the recess 2*d*. The temperature regulating block 2 is provided with a heat conduction path 8 from the temperature regulating part 3 to the recess 2*d* (that is, the reaction container 5) between the plurality of hollow parts 7*n*.

The plurality of hollow parts 7*n* are located between the temperature regulating part 3 and the recess 2*d* in the temperature regulating block 2 and extend upward from a portion of the temperature regulating block 2 in contact with the temperature regulating part 3 toward the recess 2*d*. A space between the hollow parts 7*n* extends to connect the temperature regulating part 3 and the recess 2*d* to form the heat conduction path 8 from the temperature regulating part 3 to the recess 2*d*.

The heat conduction path 8 extends upward from the bottom surface 2*e* of the temperature regulating block 2 in contact with the temperature regulating part 3, reaches the lower portion of the recess 2*d* of the temperature regulating block 2, and conducts heat of the temperature regulating part 3 to the lower portion of the recess 2*d* (that is, the lower portion of the reaction container 5). The temperature regulating block 2 is preferably provided with a plurality of heat conduction paths 8.

Note that the temperature regulating block 2 may or may not be provided with the cylindrical hollow part 7 surrounding the periphery of the recess 2*d* (or the reaction container 5).

The temperature regulating block 2 is provided with the plurality of hollow parts 7*n* at the lower portion in contact with the temperature regulating part 3, and is provided with the heat conduction path 8 extending upward from the bottom surface 2*e*. Thus, it is possible to reduce the heat capacity of the temperature regulating block 2 and to shorten the heat conduction distance from the temperature regulating part 3 to the reaction container 5. Therefore, the temperature regulating block 2 can efficiently transfer the heat generated in the temperature regulating part 3 to the reaction container 5, and can make the temperature change of the reaction container 5 faster.

Note that the present invention is not limited to the above embodiments, and various modifications are possible. For example, the above-described embodiments have been described in detail in order to describe the present invention in an easy-to-understand manner, and the present invention is not necessarily limited to an aspect including all the described configurations. Further, a part of the configuration of one embodiment can be replaced with the configuration of another embodiment. In addition, the configuration of another embodiment can be added to the configuration of one embodiment. In addition, a part of the configuration of each embodiment can be deleted, or another configuration can be added or replaced.

REFERENCE SIGNS LIST

1 temperature control device
2 temperature regulating block
2*a* upper surface measurement point
2*b* central measurement point
2*c* upper surface
2*d* recess
2*e* bottom surface
3 temperature regulating part
4 heat dissipation part
5 reaction container
6 reaction solution
7 hollow part
7*a* region having low arrangement density of hollow parts
7*b* region having high arrangement density of hollow parts
7*c* connection part
7*d* opening
7*e* region having high arrangement density of hollow parts
7*f* region having low arrangement density of hollow parts
7*g* region having low arrangement density of hollow parts
7*h* region having high arrangement density of hollow parts
7*n* hollow part
8 heat conduction path

The invention claimed is:

1. A temperature control device comprising:
   a temperature regulating block on which a container accommodating a solution is able to be placed; and
   a temperature regulating part that is installed to be in contact with the temperature regulating block and changes a temperature of the solution,
   wherein the temperature regulating block is provided with a plurality of hollow parts on an inside thereof and is provided with a recess in which the container accommodating the solution is placed, at an upper portion, and
   an arrangement density of the hollow parts varies depending on a distance from the recess.

2. The temperature control device according to claim 1, wherein
   the temperature regulating block is provided with a plurality of the hollow parts, and
   the plurality of the hollow parts communicate with each other.

3. The temperature control device according to claim 1, wherein
   the temperature regulating block is provided with a plurality of the hollow parts and an opening on a surface, and
   the plurality of the hollow parts communicate with each other, and communicate with an outside of the temperature regulating block from the opening.

4. The temperature control device according to claim 1, wherein the arrangement density is different between a portion above and a portion below a predetermined position as a position of a liquid level of the solution accommodated in the container placed in the recess.

5. The temperature control device according to claim 1, wherein the temperature regulating block is provided with a cylindrical hollow part on the inside thereof, and the cylindrical hollow part surrounds a periphery of the recess.

6. A temperature control device comprising:

a temperature regulating block on which a container accommodating a solution is able to be placed; and a temperature regulating part that is installed to be in contact with the temperature regulating block and changes a temperature of the solution, wherein the temperature regulating block is provided with a plurality of hollow parts on an inside thereof, the temperature regulating block is provided with a recess in which the container accommodating the solution is placed, at an upper portion, an arrangement density at which the hollow parts are disposed varies depending on a distance from the recess, the temperature regulating block is provided with a cylindrical hollow part on the inside thereof, and the cylindrical hollow part surrounds a periphery of the recess.

7. The temperature control device according to claim 6, wherein the temperature regulating block is provided with a plurality of the hollow parts between the temperature regulating part and the recess, each of the hollow parts extends toward the recess from a portion of the temperature regulating block, the portion being in contact with the temperature regulating part, and the hollow parts extend to connect the temperature regulating part and the recess.

* * * * *